(12) United States Patent
Shimizu et al.

(10) Patent No.: US 7,897,772 B2
(45) Date of Patent: Mar. 1, 2011

(54) ACID ADDITION SALT OF IRINOTECAN

(75) Inventors: Hideaki Shimizu, Minato-ku (JP);
Miyuki Uchida, Minato-ku (JP); Seigo Sawada, Minato-ku (JP); Norimasa Kaneda, Minato-ku (JP); Tsuneo Matsumoto, Minato-ku (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 875 days.

(21) Appl. No.: 11/576,356

(22) PCT Filed: Sep. 29, 2005

(86) PCT No.: PCT/JP2005/017999

§ 371 (c)(1),
(2), (4) Date: Aug. 7, 2007

(87) PCT Pub. No.: WO2006/038526

PCT Pub. Date: Apr. 13, 2006

(65) Prior Publication Data

US 2007/0299099 A1  Dec. 27, 2007

(30) Foreign Application Priority Data

Oct. 1, 2004 (JP) .............................. 2004-289622

(51) Int. Cl.
*C07D 401/02* (2006.01)
(52) U.S. Cl. ..................................................... 546/122

(58) Field of Classification Search .................. 514/316; 546/187, 122

See application file for complete search history.

(56) References Cited

U.S. PATENT DOCUMENTS

| 4,473,692 | A |   | 9/1984 | Miyasaka et al. |
| 4,545,880 | A |   | 10/1985 | Miyasaka et al. |
| 4,604,463 | A | * | 8/1986 | Miyasaka et al. ........... 544/125 |
| 6,294,192 | B1 | * | 9/2001 | Patel et al. .................. 424/451 |

FOREIGN PATENT DOCUMENTS

| JP | 58-39683 | 3/1983 |
| JP | 60 19790 | 1/1985 |
| JP | 61 85319 | 4/1986 |
| JP | 7-277981 | 10/1995 |
| JP | 10-17472 | 1/1998 |
| JP | 2004 277374 | 10/2004 |
| JP | 2005 168937 | 6/2005 |

* cited by examiner

*Primary Examiner*—Taofiq A Solola
(74) *Attorney, Agent, or Firm*—Oblon, Spivak, McClelland, Maier & Neustadt, L.L.P.

(57) ABSTRACT

The present invention is directed to an irinotecan acid addition salt which is formed through addition of an acid selected from the group consisting of sulfuric acid, nitric acid, phosphoric acid, methanesulfonic acid, citric acid, maleic acid, and succinic acid to irinotecan, to a method for producing the salt, and to a pharmaceutical composition containing the salt. The addition salt requires no heating process during drug preparation and provides an aqueous drug product in which the salt is stably dissolved.

3 Claims, No Drawings

ACID ADDITION SALT OF IRINOTECAN

CROSS-REFERENCE TO RELATED APPLICATIONS

This application is a 371 of PCT/JP05/17999 filed Sep. 29, 2005 and claims the benefit of JP 2004-289622 filed Oct. 1, 2004.

TECHNICAL FIELD

The present invention relates to a novel irinotecan acid addition salt which exhibits excellent solubility and peroral absorbability and which can provide a stable aqueous drug product.

BACKGROUND ART

Camptothecin (CPT) is an alkaloid contained in leaves and bark of *Camptotheca Acuminata* (Chinese origin) and other plants. Irinotecan (7-ethyl-10-[4-(1-piperidino)-1-piperidino]carboxyoxycamptothecin) hydrochloride (CPT-11) (Patent Document 1), which is a semi-synthetic derivative of camptothecin, is a particularly important substance, since the irinotecan maintains a high anti-tumor activity originating from camptothecin and exhibits reduced toxicity. CPT-11 is known to be metabolized in the body into 7-ethyl-10-hydroxycamptothecin (SN-38) (Patent Document 2), which is a semi-synthetic derivative thereby exhibits the relevant activity.

Generally, camptothecins such as CPT-11 are intravenously administered to patients in need thereof. Therefore, these compounds are commercialized as injections which have been adjusted to become isotonic by use of an agent such as sorbitol, and are employed in practice. Various attempts have been made to formulate the camptothecins into different preparations. For examples there have been known a controlled-release drug containing a camptothecin derivative incorporated into collagen-2-hydroxyethyl methacrylate copolymer (Patent Document 3) and a controlled-release drug containing a camptothecin or a derivative thereof carried by poly(lactic acid-glycolic acid) copolymer (Patent Document 4).

However, since CPT-11 has poor solubility in water, an aqueous drug product thereof needs to be prepared through heating which is not preferred. Therefore, there is demand for development of a novel irinotecan derivative which has high water solubility and which enables production of aqueous drug products without heating, for the purpose of simplifying the drug production steps.

Patent Document 1. JP-B-1991-4077
Patent Document 2: JP-B-1987-47193
Patent Document 3: JP-A-1995-277981
Patent Document 4: JP-A-1998-17472

DISCLOSURE OF THE INVENTION

Problems to be Solved by the Invention

Thus, an object of the present invention is to provide an irinotecan derivative which requires no heating process during production of aqueous drug products and which can provide drug products in which the derivative is stably dissolved in water.

Means for Solving the Problems

The present inventors have conducted extensive studies in order to attain the aforementioned object, and have found that an acid addition salt of irinotecan obtained from a specific acid exhibits excellent water solubility, and use of the acid addition salt enables production of an aqueous drug product thereof without a heating process. The inventors have also found that the irinotecan acid addition salt exhibits excellent peroral absorbability and, therefore, is useful for producing a peroral drug product.

Accordingly, the present invention provides an irinotecan acid addition salt which is formed through addition of an acid selected from the group consisting of sulfuric acid, nitric acid, phosphoric acid, methanesulfonic acid, citric acid, maleic acid, and succinic acid to irinotecan.

The present invention also provides a method for producing an irinotecan acid addition salt, the method containing suspending irinotecan in a lower alcohol, water, or an aqueous lower alcohol to thereby form a suspension; subsequently adding to the suspension an acid selected from the group consisting of sulfuric acid, nitric acid phosphoric acid, methanesulfonic acid, citric acid, maleic acid, and succinic acid, to thereby form a mixture; and subsequently, adding acetonitrile, acetone, or an acetonitrile-acetone mixed solvent to the mixture, to thereby crystallize the salt, or lyophilizing the mixture.

The present invention further provides a pharmaceutical composition containing an irinotecan acid addition salt which is formed through addition of an acid selected from the group consisting of sulfuric acid, nitric acid, phosphoric acid, methanesulfonic acid, citric acid, maleic acid, and succinic acid to irinotecan, and a pharmaceutically acceptable carrier.

Effects of the Invention

Since the irinotecan acid addition salt of the present invention has excellent water solubility, irinotecan can be dissolved in water at high concentration without performing a heating process during preparation of an aqueous drug product thereof, thereby producing a stable, high-concentration irinotecan aqueous product. In addition, the irinotecan acid addition salt of the present invention has excellent peroral absorbability, and can be made into a peroral drug product.

BEST MODES FOR CARRYING OUT THE INVENTION

The irinotecan acid addition salt of the present invention encompasses an irinotecan sulfuric acid salt, an irinotecan nitric acid salt, an irinotecan phosphoric acid salt, an irinotecan methanesulfonic acid salt, an irinotecan citric acid salt, an irinotecan maleic acid salt, and an irinotecan succinic acid salt. Among these irinotecan acid addition salts, an irinotecan sulfuric acid salt and an irinotecan methanesulfonic acid salt are particularly preferred, since these salts can be yielded as crystals and exhibit high water solubility.

The irinotecan acid addition salt of the present invention can be produced through, for example, a process including suspending in a lower alcohol, water, or an aqueous lower alcohol; subsequently, adding an acid selected from the group consisting of sulfuric acid, nitric acid, phosphoric acid, methanesulfonic acid, citric acid, maleic acid, and succinic acid to the suspension, to thereby form a mixture; and subsequently, adding to the mixture acetonitrile, acetone, or an acetonitrile-acetone mixed solvent, to thereby crystallize the salt, or lyophillzing the mixture.

The lower alcohol employed in the invention is preferably a C1 to C5 alcohol, more preferably a C1 to C3 alcohol, with methanol being particularly preferred. No particular limitation is imposed on a mixing ratio between lower alcohol and water in the aqueous lower alcohol, and the mixing ratio of lower alcohol to water by weight is preferably 1:4, more preferably 1:1. It is preferable that 0.05 to 50 mL, more preferably 0.1 to 10 mL of the solvent for formation of the acid addition salt, which is a lower alcohol water, or an aqueous lower alcohol is used with respect to 1 g of irinotecan.

Theoretically, the acid is added in a quantity equimolar to the amount of irinotecan. From the viewpoint of yield and other factors the amount of acid is preferably 1.0 to 1.2 eq., more preferably 1.0 to 1.05 eq.

No particular limitation is imposed on the conditions under which mixing of irinotecan and acid is performed. For example, the solvent is stirred at 0 to 40° C. (preferably 5 to 30° C.) until irinotecan is dissolved in the solvent. In the case where the acid is theoretically added in a quantity equimolar or more with respect to the amount (1 g) of irinotecan, stirring is preferably performed at 5 to 30° C. within two hours, more preferably within one hour.

After mixing of irinotecan and the aforementioned acid, crystallization solvent is added to the mixture, to thereby crystallize the target irinotecan acid addition salt, or the reaction mixture for salt formation is lyophilized, whereby the irinotecan acid addition salt of interest can be produced.

The amount of the solvent added to crystallize acid-added irinotecan, which solvent is acetonitrile, acetone, or an acetonitrile-acetone mixed solvent, is preferably 1 to 300 mL, more preferably 15 to 170 mL, with respect to 1 g of irinotecan. No particular limitation is imposed on the mixing ratio between acetonitrile and acetone, and the mixing ratio by weight of acetonitrile to acetone is preferably 1:1, more preferably 1:2.

In a preferred mode, crystallization is performed at 20 to 30° C. for 20 to 30 hours, more preferably at 25° C. for 24 hours, under stirring. In order to accelerate crystallization a seed crystal of a corresponding irinotecan acid addition salt may be added. Specifically; in the case where an irinotecan sulfuric acid salt is crystallized, a seed crystal of the irinotecan sulfuric acid salt is added to the solution. The thus-formed irinotecan acid addition salt is separated through filtration by filter paper, a membrane filter, etc., and, if needed, the salt may be dried at 15 to 25° C. and additionally at room temperature under vacuum, for example, with an evacuation pump. No particular limitation is imposed on the drying conditions, and drying may be performed at room temperature under a reduced pressure of 2 to 6 mmHg (preferably 4 mmHg).

No particular limitation is imposed on the method of lyophilization, and any conventional method may be employed. Preferably, a frozen solution is dried by means of a freeze-drying apparatus at 15 to 25° C., more preferably at room temperature. Specifically lyophylization may be performed at room temperature under reduced pressure at 0.05 Torr (i.e., approximately equivalent 0.05 mmHg).

An irinotecan sulfuric acid salt is preferably produced through, sequentially, suspending irinotecan in a lower alcohol, adding sulfuric acid to the suspension to thereby form a mixture, and adding to the mixture acetonitrile or acetone to thereby crystallize the salt.

An irinotecan methanesulfonic acid salt is preferably produced through, sequentially, suspending irinotecan in water or an lower alcohol, adding methanesulfonic acid to the suspension to thereby form a mixture, and adding acetone to the mixture to thereby crystallize the salt.

The thus-produced irinotecan acid addition salt of the present invention exhibits high water solubility and excellent peroral absorbability. Therefore, a pharmaceutical composition containing the irinotecan acid addition salt and a pharmaceutically acceptable carrier is useful as an injection aqueous product, a peroral drug product, and other drug products. In the case where an aqueous drug product is prepared, examples of the pharmaceutically acceptable carrier employed include purified water, physiological saline, a pH-modifier, a tonicity agent, a stabilizer, and a buffer. In the case where a peroral drug product is prepared, examples of the pharmaceutically acceptable carrier include an excipient, a lubricant, a binder, a disintegrant, a colorant, a taste-controlling agent, and a flavoring agent. The peroral product may be in the form of, for example, tablet, granules, powder, capsule.

By virtue of excellent malignant tumor treatment effect of irinotecan the pharmaceutical composition of the present invention containing the irinotecan acid addition salt can serve as a pharmaceutical composition for the treatment of a malignant tumor. Examples of the target malignant tumor include lung cancer, uterine cancer, ovary cancer, stomach cancer, colorectal cancer, breast cancer, lymphoma, and pancreas cancer.

In the case where an aqueous drug product is prepared from the irinotecan acid addition salt of the present invention, the aqueous drug product preferably has a pH of 3.0 to 4.0, more preferably 3.4 to 3.6, at room temperature (25° C.). Preferably, pH control is performed by use of an acid such as sulfuric acid, phosphoric acid, methanesulfonic acid, or citric acid, or an alkali such as sodium hydroxide, sodium carbonate, or sodium hydrogencarbonate.

In the case of an aqueous drug product of the irinotecan acid addition salt of the present invention, a high-concentration aqueous product of the irinotecan acid addition salt may be produced, and the aqueous product is diluted upon use. The aqueous drug product is preferably an injection, more preferably an intravenous in reaction. When the infection is prepared, additional ingredients may be employed with the aforementioned ingredient Examples of the additional ingredients include distilled water for injections; sugars such as glucose, mannose, and lactose; inorganic salts such as sodium chloride and phosphoric acid salts; organic amines such as HEPES and PIPES; and other common ingredients for injections such as a stabilizer, an excipient, and a buffer. The irinotecan acid addition salt content of the injection upon use is preferably 1 to 50 mg/mL as irinotecan, particularly preferably 10 to 30 mg/mL.

EXAMPLES

The present invention will next be described in more detail by way of examples, which should not be construed as limiting the invention thereto.

Example 1

To an aqueous suspension of irinotecan (1-ethyl-10-[4-(1-piperidino)-1-piperidino]carbonyloxycamptothecin) produced through the method disclosed in Patent Document 1, each acid species was added, to thereby produce a corresponding irinotecan acid addition salt. The irinotecan acid addition salt content was adjusted to 100 mg/mL. When sulfuric acid, phosphoric acid, methanesulfonic acid, citric acid, maleic acid, or succinic acid was employed, the salt was dissolved in water at room temperature, to thereby form an aqueous solution of the acid added salt, whereas when hydrochloric acid nitric acid, hydrobromic acid, acetic acid, or fumaric acid was employed, the salt was not dissolved in water at room temperature, and the suspension was maintained. Each of the aqueous solutions employing sulfuric acid, phosphoric acid methanesulfonic acid, citric acid, maleic acid, and succinic acid, respectively, was filtered by a membrane filter, and the filtrate was stirred at room temperature (25° C.). After continuous stirring for 6 days, the aqueous solution was visually observed so as to evaluate the state of the solution. The results are shown in Table 1.

TABLE 1

|  | State of the Solution after Day 6 |
|---|---|
| Irinotecan sulfuric acid addition salt | No crystal deposited |
| Irinotecan phosphoric acid addition salt | No crystal deposited |
| Irinotecan methanesulfonic acid addition salt | No crystal deposited |
| Irinotecan citric acid addition salt | No crystal deposited |
| Irinotecan maleic acid addition salt | No crystal deposited |
| Irinotecan succinic acid addition salt | No crystal deposited |
| Irinotecan nitric acid addition salt | *1 |
| Irinotecan hydrobromic acid addition salt | *1 |
| Irinotecan acetic acid addition salt | *1 |
| Irinotecan fumaric acid addition salt | *1 |
| Irinotecan hydrochloric acid addition salt | *1 |

1*: The formed irinocecan acid addition salt was not dissolved in water at room temperature.

Example 2

In a manner similar to that of Example 1, an irinotecan nitric acid addition salt, an irinotecan hydrobromic acid addition salt, and an irinotecan acetic acid addition salt were prepared so that each solution had a concentration of 100 mg/mL. When these solutions were heated, the irinotecan nitric acid addition salt was completely dissolved at 70° C. under stirring for three minutes. In contrast, the irinotecan hydrobromic acid addition salt and the irinotecan acetic acid addition salt were maintained undissolved in respective liquids, even when these liquids had been stirred at 100° C. for 30 minutes. The thus-produced irinotecan nitric acid addition salt solution was stirred at 25° C. After stirring of the solution for about 42 hours, crystals of the irinotecan nitric acid addition salt were deposited.

Example 3

A 1-mol/L sulfuric acid (1 eq.) was added to an irinotecan methanol suspension, to thereby dissolve irinotecan. Acetonitrile or acetone, serving as a crystallization solvent, was added to the solution. The liquid was allowed to stand at room temperature for 20 hours and filtered, to thereby collect an irinotecan sulfuric acid addition salt. Table 2 shows the results

TABLE 2

| No. | Irinotecan (g) | Methanol (mL/g-irinotecan) | Crystallization solvent (mL/g-irinotecan) | | Recovery (%) |
|---|---|---|---|---|---|
|  |  |  | Acetonitrile | Acetone |  |
| 1 | 1.0 | 1.6 | 27 | — | 68 |
| 2 | 0.9 | 5.0 | 66 | — | 70 |
| 3 | 1.0 | 8.3 | 100 | — | 52 |

TABLE 2-continued

| No. | Irinotecan (g) | Methanol (mL/g-irinotecan) | Crystallization solvent (mL/g-irinotecan) | | Recovery (%) |
|---|---|---|---|---|---|
|  |  |  | Acetonitrile | Acetone |  |
| 4 | 1.0 | 1.6 | — | 16.5 | 93 |
| 5 | 0.9 | 5.0 | — | 33 | 91 |
| 6 | 1.0 | 8.3 | — | 20 | 81 |
| 7 | 10.0 | 1.6 | — | 16.5 | 93 |
| 8 | 10.0 | 8.3 | — | 20 | 80 |

Through element analysis, the irinotecan sulfuric acid addition salt (sample No. 4) was found to contain carbon 56.232% (calculated: 56.399%), hydrogen 6.003 (calculated: 6.024%, and nitrogen 7.612% (calculated: 7.972%).

The thus-produced 100-mg/mL aqueous solution of irinotecan sulfuric acid addition salt was stable at room temperature (25° C.) during storage for three months, and the solution remained clear after the storage.

Example 4

In a manner similar to that of Example 3 an irinotecan methanesulfonic acid addition salt was produced. Table 3 shows the results.

TABLE 3

| No. | Irinotecan (g) | Acid addition salt formation solvent (mL) | | Crytallization solvent (mL) | Recovery (%) |
|---|---|---|---|---|---|
|  |  | Water | Methanol | Acetone |  |
| 9 | 1.0 | 1.6 | — | 166.5 | 58 |
| 10 | 1.0 | — | 1.6 | 166.5 | 61 |
| 11 | 1.0 | — | 1.6 | 83.3 | 63 |

The thus-produced 100-mg/mL aqueous solution of irinotecan methanesulfonic acid addition salt was stable at room temperature (25° C.) during storage for one month, and the solution remained clear after the storage.

Example 5

Each of the following aqueous solutions (20, 30, and 40 mg/mL) of the irinotecan acid addition salts was filtered through a membrane filter, and the filtrate was poured into a glass vessel. The filtrate was allowed to stand at room temperature for three months, and the aqueous solution after storage was visually observed so as to evaluate the solution state. The results are shown in Table 4.

TABLE 4

| Irinotecan acid addition salt (Production method) | Concentration (mg/mL) | | |
|---|---|---|---|
|  | 20 | 30 | 40 |
| Nitric acid addition salt (1) | – | – | + |
| Nitric acid addition salt (2) | – | – | – |
| Sulfuric acid addition salt (2) | – | – | – |
| Phosphoric acid addition salt (2) | – | – | – |

Note:
Production method (1): Similar to that of Example 2
Production method (2): Adding acid (1.0 eq.) to aqueous irinotecan suspension, followed by lyophilizing the mixture.
Remarks:
–: No crystal deposition observed.
+: Not completely dissolved during preparation.

All the irinotecan acid addition salts falling within the scope of the present invention were stable for a long period of time. Irinotecan acid addition salts produced through lyophilization were found to be more stable in aqueous solution.

Example 6

Peroral absorbability of the produced irinotecan acid addition salts were evaluated through the following method (1) Irinotecan acid addition salts:
Irinotecan sulfuric acid addition salt (present invention)
Irinotecan methanesulfonic acid addition salt (present invention)
Irinotecan hydrochloric acid addition salt (Comparative Example)

(2) Animal

Male beagles (conditioning started at 8 to 9 months of age, body weight of 1.2 to 13.2 kg) had been conditioned for one week before experiments. During the period from one day before the day of initial administration to one day before the day of final (6th) administration, the body weights were within a range of 11.5 to 15.3 kg. To each beagle, a solid chow (about 350 g) was fed once a day at around 3 p.m., and the unconsumed chow was removed at around 9 a.m. on the following day, except that on the day before the day of administration the unconsumed chow was removed about two hours after feeding. On the day of administration, blood was drawn three hours after administration and the chow was fed after blood collection. On the day after the day of administration, the unconsumed chow was removed at 9 a.m.

(3) Administration

Through the cross-over method including a 2-week rest period, each irinotecan acid addition salt was charged into gelatin capsules (½ ounces), and the encapsulated drugs were perorally administered to each beagle five times. The dose was 10 mg/kg as irinotecan.

On the basis of the body weight of each beagle weighed before administration on each day of administration, the tested salts were charged into gelatin capsules in such amounts that the dose of irinotecan was adjusted to 10 mg/kg in each beagle. The amount of required camptothecin (injection) and that of the irinotecan hydrochloric acid addition salt were calculated on the basis of the amount of the irinotecan hydrochloric acid addition salt being regarded as 100%, whereas the amounts of required other irinotecan acid addition salts were calculated with the assumption that the purity of these salts is 100%. Capsule drugs containing each irinotecan acid addition salt were forcedly, perorally administered to each beagle. After administration, tap water (about 20 mL) was fed to the mouth of the beagle by use of an injection syringe.

(4) Blood collection: By use of an injection syringe which had been subjected to an anti-coagulation treatment with heparin sodium solution, blood was drawn through the antebrachial cephalic vein. The thus-collected blood samples were dispensed into 1.5-mL tubes, to which heparin sodium (20 μL, 20 units) had been added in advance and which had been dried under nitrogen flow (tubes employed for the first administration were not dried). The samples were centrifuged (4° C., about 13,000×g, one minute) to thereby obtain plasma. An aliquot (about 0.3 mL) was collected from each sample, and placed in a storage vessel immediately, an equivolume of 0.146-mol/L phosphoric acid (phosphoric acid 100-fold diluted with injection water) was added to the plasma, followed by stirring.

(5) Determination of irinotecan level

The fluorescence HPLC method (Kurita et al., J. Chromatogr. B. 724, 335-344, 1993) was adopted. The lower quantification limit was 5 mg/mL plasma.

(6) Pharmacokinetic analysis of irinotecan

Non-compartmental analysis of the obtained data was performed by use of a WinNonlin Ver4.1. Data of the following pharmacokinetic parameters were obtained.

Final phase half-time ($T_{1/2}$),
Time to reach maximum plasma level ($T_{max}$),
Maximum plasma level ($C_{max}$),
Area under time-level curve to infinite time ($AUC_{0\text{-}inf}$),
Bioavailability (BA), wherein BA(%)=($AUC_{0\text{-}inf}$ of irinotecan after oral administration)÷($AUC_{0\text{-}inf}$ of irinotecan after intravenous injection)×100, and Mean absorption time (MAT), wherein MAT(h)=(mean residence time ($MRT_{0\text{-}inf}$) after oral administration)−(mean residence time ($MRT_{0\text{-}inf}$) after intravenous injection).

Table 5 shows change in plasma irinotecan level after administration of irinotecan acid addition salts, and Table 6 shows the results of pharmacokinetic analysis. In the Tables, the data are represented by "mean value (n=6)±standard deviation." Only in the case where four or more animals of a group consisting of six beagles exhibited a plasma irinotecan level equal to or higher than the lower quantification limit, the level under the lower quantification limit is considered zero, to thereby calculate a mean value and standard deviation.

TABLE 5

(μg-Irinotecan/mL)

| | Peroral administration | | |
|---|---|---|---|
| Time | Irinotecan hydrochloric acid addition salt | Irinotecan sulfuric acid addition salt | Irinotecan methanesulfonic acid addition salt |
| 2 min | ND[a] | ND | ND |
| 5 | ND | ND | ND |
| 10 | —[b] | 0.126 ± 0.112 | — |
| 20 | — | 1.56 ± 1.55 | — |
| 30 | 0.254 ± 0.323 | 1.87 ± 1.32 | 1.15 ± 1.18 |
| 45 | 0.684 ± 0.557 | 2.55 ± 0.92 | 1.80 ± 1.17 |
| 1 h | 1.08 ± 0.56 | 3.07 ± 0.66 | 2.45 ± 0.90 |
| 2 | 1.59 ± 0.64 | 3.44 ± 0.62 | 3.22 ± 0.71 |
| 3 | 2.01 ± 0.45 | 3.05 ± 0.45 | 2.90 ± 0.52 |
| 4 | 1.62 ± 0.39 | 2.16 ± 0.27 | 2.24 ± 0.42 |
| 6 | 0.947 ± 0.363 | 1.09 ± 0.12 | 1.08 ± 0.19 |
| 8 | 0.538 ± 0.264 | 0.507 ± 0.049 | 0.513 ± 0.094 |
| 12 | 0.179 ± 0.138 | 0.147 ± 0.033 | 0.142 ± 0.033 |
| 24 | 0.0374 ± 0.0444 | 0.0138 ± 0.044 | 0.0144 ± 0.060 |

[a]Blood collection was not performed.
[b]≧3 Beagles of a group consisting of six beagles exhibited a plasma level of ≦5 ng/mL.

TABLE 6

| | Peroral administration | | |
|---|---|---|---|
| Parameters | Irinotecan hydrochloric acid addition salt | Irinotecan sulfuric acid addition salt | Irinotecan methanesulfonic acid addition salt |
| $T_{1/2}$ (h) | 3.81 ± 1.22(5) | 3.68 ± 0.12(5) | 3.59 ± 0.33(6) |
| $T_{max}$ (h)[a] | 2.83 ± 0.41(6) | 2.33 ± 0.52(6) | 2.17 ± 0.41(6) |
| $C_{max}$ (μg/mL) | 2.03 ± 0.45(6) | 3.67 ± 0.38(5)$ | 3.47 ± 0.41(5)$ |
| $AUC_{0-inf}$ (μg·h/mL) | 11.23 ± 1.59(5) | 18.54 ± 1.59(5)$ | 17.58 ± 2.08(5)$ |
| BA (%) | 48.80 ± 10.97(6) | 70.14 ± 9.58(6)# | 60.96 ± 3.84(5) |
| MAT (h) | 2.12 ± 0.78(5) | 0.78 ± 0.48(5)# | 1.01 ± 0.32(5)* |

Note: Mean value ± standard deviation, calculated excluding values under quantification limit. Numerals in parentheses indicate the number of samples statistically processed. Irinotecan level data are those of the base form of irinotecan
*p ≦ 0.05, #p ≦ 0.01, and $p ≦ 0.001
[a]$T_{max}$ was not statistically processed.

In the oral administration groups, although considerable variation between specimens was observed, the irinotecan sulfuric acid addition salt exhibited an increase in plasma irinotecan level immediately after administration, and the level became measurable 10 minutes after administration. Twenty minutes after administration, the level increased to 1.56 μg/mL and maintained a level ≧3 μg/mL from hour 1 to hour 3. The irinotecan methanesulfonic acid addition salt exhibited a rapid increase in plasma level, and the plasma level reached the maximum two hours after administration. Thereafter, the level decreased, similar to the case of the irinotecan sulfuric acid addition salt.

Maximum plasma level of the irinotecan hydrochloric acid addition salt was 2.03 μg/mL, whereas that of the irinotecan sulfuric acid addition salt was 3.67 μg/mL, and that of the irinotecan methanesulfonic acid addition salt was 3.47 μg/mL. Statistically significant differences were observed at a significance level of 0.1%.

The area under the time-level curve to infinite time ($AUC_{0-inf}$) of the irinotecan hydrochloric acid addition salt was 11.23 μg·h/mL, whereas that of the irinotecan sulfuric acid addition salt was 13.54 μg·h/mL and that of the irinotecan methanesulfonic acid addition salt was 17.68 μg·h/mL. Statistically significant differences were observed at a significance level of 0.1%.

Bioavailability (BA) of the irinotecan hydrochloric acid addition salt was 48.80%, whereas that of the irinotecan sulfuric acid addition salt was 70.14%. A statistically significant difference was observed at a significance level of 1%.

Mean absorption time (MAT) of the irinotecan hydrochloric acid addition salt was 2.12 hours, whereas that of the irinotecan sulfuric acid addition salt was 0.78 hours and that of the irinotecan methanesulfonic acid addition salt was 1.01 hours. Statistically significant differences were observed at significance levels of 1% and 5%, respectively.

The invention claimed is:

1. A method for producing an irinotecan acid addition salt with an acid selected from the group consisting of sulfuric acid, nitric acid, phosphoric acid, methanesulfonic acid, citric acid, maleic acid, and succinic acid to irinotecan, the method comprising suspending irinotecan in a lower alcohol, water, or an aqueous lower alcohol, to thereby form a suspension; subsequently, adding to the suspension an acid selected from the group consisting of sulfuric acid, nitric acid, phosphoric acid, methanesulfonic acid, citric acid, maleic acid, and succinic acid, to thereby form a mixture; and subsequently, adding acetonitrile, acetone, or an acetonitrile-acetone mixed solvent to the mixture, to thereby crystallize the salt, or lyophilizing the mixture.

2. A method for producing an irinotecan sulfuric acid addition salt comprising suspending irinotecan in a lower alcohol, to thereby form a suspension; subsequently, adding sulfuric acid to the suspension, to thereby form a mixture; and subsequently, adding acetonitrile, acetone, or an acetonitrile-acetone mixed solvent to the mixture, to thereby crystallize the salt.

3. A method for producing an irinotecan methanesulfonic acid addition salt comprising suspending irinotecan in water or a lower alcohol, to thereby form a suspension; subsequently, adding methanesulfonic acid to the suspension, to thereby form a mixture; and subsequently, adding acetone, to the mixture, to thereby crystallize the salt.

* * * * *